United States Patent
Rhead et al.

(10) Patent No.: US 11,428,576 B2
(45) Date of Patent: Aug. 30, 2022

(54) SYSTEMS AND METHODS OF DETECTING FLAME OR GAS

(71) Applicant: Carrier Corporation, Palm Beach Gardens, FL (US)

(72) Inventors: Jamie Rhead, Plymouth, MN (US); Dayne Plemmons, Minneapolis, MN (US); Anand Venkatesh Sankarraj, Eden Prairie, MN (US); Theodore Hermann, Eden Prairie, MN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 0 days.

(21) Appl. No.: 17/098,798

(22) Filed: Nov. 16, 2020

(65) Prior Publication Data

US 2021/0156741 A1    May 27, 2021

Related U.S. Application Data (60) Provisional application No. 62/939,281, filed on Nov. 22, 2019.

(51) Int. Cl.
*H01L 31/00*     (2006.01)
*G01J 5/00*      (2022.01)
(Continued)

(52) U.S. Cl.
CPC ........ *G01J 5/0018* (2013.01); *G01N 33/0027* (2013.01); *G06V 20/00* (2022.01); *G01J 2005/0077* (2013.01)

(58) Field of Classification Search
CPC .. G01J 5/0018; G01J 2005/0077; G01J 1/429; G01J 5/0014; G01J 5/025;
(Continued)

(56) References Cited

U.S. PATENT DOCUMENTS

| 5,153,722 A | 10/1992 | Goedeke et al. |
| 6,518,574 B1 | 2/2003 | Castleman |

(Continued)

FOREIGN PATENT DOCUMENTS

| CN | 102708647 A | 10/2012 |
| CN | 102760230 A | 10/2012 |

(Continued)

OTHER PUBLICATIONS

European Search Report for Application No. 20208759.9; dated Apr. 21, 2021; 12 Pages.

*Primary Examiner* — Kiho Kim
(74) *Attorney, Agent, or Firm* — Cantor Colburn LLP (57) ABSTRACT

A flame or gas detection method includes determining non-imaging sensor system detection state for a scene of interest, determining an imaging sensor system detection state for the scene of interest, and validating one of the non-imaging sensor system detection state and the imaging sensor system detection state with the other of the non-imaging sensor system detection state and the imaging sensor system detection state. A flame or gas detecting system detection state is then indicated at a user interface including the validated one of the non-imaging sensor system detection state and the imaging system detection state. Flame or gas detection systems and computer program products are also described.

19 Claims, 5 Drawing Sheets

(51) Int. Cl.
*G01N 33/00* (2006.01)
*G06V 20/00* (2022.01)

(58) Field of Classification Search
CPC ........ G01J 5/0846; G01J 5/0859; G01J 5/602; G01N 33/0027; G06V 20/00
See application file for complete search history.

(56) References Cited

U.S. PATENT DOCUMENTS

| | | |
|---|---|---|
| 7,202,794 B2 | 4/2007 | Huseynov et al. |
| 8,655,010 B2 | 2/2014 | Finn et al. |
| 8,841,617 B2 | 9/2014 | Cole |
| 9,733,129 B1 | 8/2017 | Au et al. |
| 2011/0304728 A1 | 12/2011 | Owrutsky et al. |
| 2013/0286213 A1 | 10/2013 | Cetin et al. |
| 2017/0227400 A1* | 8/2017 | Boroojeny ............ G01J 5/0018 |
| 2021/0208001 A1* | 7/2021 | Kim ...................... G01J 5/0018 |

FOREIGN PATENT DOCUMENTS

| | | | |
|---|---|---|---|
| CN | 103680034 A | | 3/2014 |
| EP | 1233386 A2 | | 8/2002 |
| EP | 3407034 A1 | | 11/2018 |
| KR | 1767980 B1 | * | 8/2017 |

* cited by examiner

| EXAMPLE SYSTEM STATES | APPROPRIATE ACTIONS |
|---|---|
| MWIR INDICATES NO FLAME. <br> IR IMAGER INDICATES NO SOURCES RADIANT ENOUGH TO BE FLAME CANDIDATES. <br> VL IMAGER INDICATES NO VISIBLE SOURCES INTENSE ENOUGH TO BE FLAME CANDIDATES. | SUB-SYSTEMS ARE IN AGREEMENT. THERE IS NO FLAME TO ALARM. |
| MWIR DETECTS FLAME <br> IR IMAGER INDICATES AT LEAST ONE SOURCE CONFIRMED AS FLAME, AND IN A 'KEEP-IN' REGION. <br> VL IMAGER INDICATES AT LEAST ONE SOURCE CONFIRMED AS FLAME, AND IN A 'KEEP-IN' REGION. | SUB-SYSTEMS ARE IN AGREEMENT. THERE IS A FLAME TO ALARM. THE IMAGERS CONFIRM THE FLAME AND PROVIDE THE LOCATION WHICH MAY BE INDICATED ON A DISPLAY TO THE END-USER. |
| MWIR DETECTS FLAME <br> IR IMAGER INDICATES AT LEAST ONE SOURCE CONFIRMED AS FLAME, AND IN A 'KEEP-IN' REGION. <br> VL IMAGER INDICATES NO VISIBLE SOURCES INTENSE ENOUGH TO BE FLAME CANDIDATES. | ANALYZE THE MWIR SPECTRAL CHARACTERISTICS OF THE FLAME TO DETERMINE WHETHER IT IS OF A TYPE THAT MAY BE DIFFICULT TO SEE VISUALLY. IF SO THEN THE ABSENCE OF FLAME DETECTION BY THE VL IMAGER SHOULD BE DISREGARDED. THE IR IMAGER VERIFIES THAT THE DETECTED FLAME IS IN A 'KEEP-IN' REGION. |
| MWIR DETECTS FLAME <br> IR IMAGER INDICATES AT LEAST ONE SOURCE CONFIRMED AS FLAME, BUT NO SUCH SOURCES IN 'KEEP-IN' REGIONS. <br> VL IMAGER INDICATES AT LEAST ONE SOURCE CONFIRMED AS FLAME, BUT NO SUCH SOURCES IN 'KEEP-IN' REGIONS. | COMPARE THE TIME-FREQUENCY PATTERN OF THE FLAME DETECTED BY MWIR TO THE FLAMES DETECTED BY THE IR AND VL IMAGERS. IF IT IS CERTAIN THAT THE ONLY FLAMES IN THE SCENE ARE IN THE 'KEEP-OUT' REGIONS, THEN THE MWIR FLAME DETECTION MAY BE DISREGARDED. |
| MWIR DETECTS FLAME <br> IR IMAGER INDICATES AT LEAST ONE SOURCE RADIANT ENOUGH TO BE A FLAME CANDIDATE, BUT NO SOURCES CONFIRMED AS FLAME. <br> VL IMAGER INDICATES AT LEAST ONE SOURCE INTENSE ENOUGH TO BE A FLAME CANDIDATE, BUT NO SOURCES CONFIRMED AS FLAME. | USE THE CHARACTERISTICS OF THE MWIR FLAME DETECTION TO AID IN LOCATING THE FLAME WITHIN THE IMAGERY. COMPARE THE TEMPORAL FREQUENCY CHARACTERISTICS OF THE MWIR DETECTION TO THAT OF REGIONS OF THE IMAGERY. USE THE MWIR SPECTRAL CHARACTERISTICS OF THE DETECTION TO PREDICT THE LIKELY RADIANT INTENSITY AND COLOR OF THE FLAME AS IT MIGHT APPEAR IN THE IMAGERY. |

SYSTEMS AND METHODS OF DETECTING FLAME OR GAS

CROSS-REFERENCE TO RELATED APPLICATIONS

This application claims the benefit of Provisional Application No. 62/939,281 filed Nov. 22, 2019, the disclosure of which is incorporated herein by reference in its entirety.

BACKGROUND

The present disclosure generally relates to flame and gas detection, and more particularly to flame and gas detection using both imaging sensors and non-image sensors.

Detectors, such as sensors and imagers, are commonly used to monitor protected spaces for the presence of flame or gas. Sensors, such as mid-wave infrared non-imaging sensors, generally employ two or more sensor components with a common field of view which have filters tuned to admit electromagnetic radiation within different portions of the mid-wave infrared waveband, i.e., wavelengths between about 2.5 microns and about 5 microns. In flame detection applications, data from the sensors is analyzed to determine whether a flame is emitting electromagnetic radiation within one or more of the portions of the mid-wave infrared waveband admitted to the sensors by the spectral filters. In gas detection applications, data from the sensors is analyzed to determine whether gas within the common field of view of the sensor is absorbing electromagnetic radiation within one or more of the portions of mid-wave infrared waveband admitted to the sensors by the spectral filters. Such sensors are generally unable to spatially locate the flame or gas within the field of view of the sensor.

Imagers, such as visible, ultraviolet, or infrared imagers, generally employ a focal plane array sensitized to generate image data using electromagnetic radiation within their respective wavebands, (i.e. the visible waveband, with wavelengths from about 0.4 to 0.7 microns, the ultraviolet waveband, from between about 10 nanometers and about 400 nanometers, or the near-infrared, short-wave-infrared, mid-infrared, or long-infrared wavebands, with wavelengths between about 0.7 to 1.2 microns, about 1.2 to 2.5 microns, about 2.5 to 5 microns, and about 8 to 15 microns, respectively.) In flame detection applications the image data is analyzed to determine whether a flame within the field of view of the imaging sensor is emitting electromagnetic radiation in the waveband to which the focal plane array is sensitized. In gas detection applications the image data is analyzed to determine whether gas within the field of view of the sensor is absorbing electromagnetic radiation in the waveband to which the focal plane array is sensitized. Imagers can be prone to false alarms and/or can have difficulty discerning certain flames or gases within the field of view of the imager. However, imagers of different types have different strengths for discerning various flame or gas types under various conditions. For example, a visible imager may have difficulty discerning translucent flames, whereas an infrared imager may discern such flames more easily.

Such systems and methods have generally been acceptable for their intended purpose. However, there remains a need for improved flame and gas detectors, methods of flame and gas detection, and algorithms for detecting and validating the presence of flame or gas in a scene of interest, in order to reduce the risk of false alarm events as well as provide greater reliability than current flame or gas detectors.

BRIEF DESCRIPTION

A flame or gas detection method is provided. A flame or gas detection method includes determining non-imaging sensor system detection state for a scene of interest, determining an imaging sensor system detection state for the scene of interest, and validating one of the non-imaging sensor system detection state and the imaging sensor system detection state with the other of the non-imaging sensor system detection state and the imaging sensor system detection state. A flame or gas detecting system detection state is then indicated at a user interface including the validated one of the non-imaging sensor system detection state and the imaging system detection state.

In addition to one or more of the features described above, or as an alternative, further embodiments of the flame or gas detection method may include that determining the non-imaging sensor system detection state includes receiving non-imaging sensor data for the scene of interest; receiving non-imaging sensor system reference data for the scene of interest; and determining the non-imaging sensor system detection state based on the non-imaging sensor data and the non-imaging sensor system reference data for the scene of interest.

In addition to one or more of the features described above, or as an alternative, further embodiments of the flame or gas detection method may include that generating the non-imaging sensor data from electromagnetic radiation incident on a non-imaging sensor in a mid-wave infrared waveband or an ultraviolet waveband.

In addition to one or more of the features described above, or as an alternative, further embodiments of the flame or gas detection method may include that receiving a non-imaging sensor system health state, wherein the validating one of the non-imaging sensor system detection state and the imaging sensor system detection state with the other of the non-imaging sensor system detection state and the imaging sensor system detection state is based on the non-imaging sensor system health state.

In addition to one or more of the features described above, or as an alternative, further embodiments of the flame or gas detection method may include that determining the imaging sensor system detection state includes receiving image data from an imaging sensor for the scene of interest; receiving imaging sensor system reference data for the scene of interest; receiving an imaging sensor system keep-out definition for the scene of interest; and determining the imaging sensor system detection state based on the image data from the imaging sensor, the imaging sensor system reference data, and the imaging sensor system keep-out definition for the scene of interest.

In addition to one or more of the features described above, or as an alternative, further embodiments of the flame or gas detection method may include that generating the image data from electromagnetic radiation incident on an imaging sensor in an infrared waveband or a visible light waveband.

In addition to one or more of the features described above, or as an alternative, further embodiments of the flame or gas detection method may include that validating one of the non-imaging sensor system detection state and the imaging sensor system detection state with the other of the non-imaging sensor system detection state and the imaging sensor system detection state is based on the imaging sensor system keep-out definition for the scene of interest.

In addition to one or more of the features described above, or as an alternative, further embodiments of the flame or gas detection method may include that validating one of the non-imaging sensor system detection state and the imaging sensor system detection state with the other of the non-imaging sensor system detection state and the imaging sensor system detection state is based on the imaging sensor system health state.

In addition to one or more of the features described above, or as an alternative, further embodiments of the flame or gas detection method may include that the non-imaging sensor system detection state and the imaging sensor detection state are a non-imaging sensor system flame detection state and an imaging sensor system flame detection state.

In addition to one or more of the features described above, or as an alternative, further embodiments of the flame or gas detection method may include that the non-imaging sensor system detection state and the imaging sensor system detection state are a non-imaging sensor system gas detection state and an imaging sensor system gas detection state.

A flame or gas detection system is also provided. A flame or gas detection system includes a non-imaging sensor system with a non-imaging sensor field of view including a scene of interest; an imaging sensor system with an imaging sensor field of view including the scene of interest; and a processor. The processor is disposed in communication with the non-imaging sensor system, the imaging sensor system, and a memory having instructions recorded on the memory that, when executed by the processor, cause the processor to determine a non-imaging sensor system detection state for the scene of interest; determine an imaging sensor system detection state for the scene of interest; validate one of the non-imaging sensor system detection state and the imaging sensor system detection state with the other of the non-imaging sensor system detection state and the imaging sensor system detection state; and indicate, at a user interface operatively associated with the processor, a flame or gas detection system detection state comprising the validated one of the non-imaging sensor system detection state and the imaging sensor system detection state.

In addition to one or more of the features described above, or as an alternative, further embodiments of the flame or gas detection system may include that the instructions further cause the processor to determine the non-imaging sensor system detection state by receiving non-imaging sensor data from a non-imaging sensor for the scene of interest; receiving non-imaging sensor reference data for the scene of interest; and determining the non-imaging sensor system detection state based on the non-imaging sensor data and the non-imaging sensor reference data for the scene of interest.

In addition to one or more of the features described above, or as an alternative, further embodiments of the flame or gas detection system may include that the non-imaging sensor is a mid-wave infrared waveband sensor or an ultraviolet waveband sensor.

In addition to one or more of the features described above, or as an alternative, further embodiments of the flame or gas detection system may include that the instructions further cause the processor to receive a non-imaging sensor system health state, wherein the processor validates the one of the non-imaging sensor system detection state and the imaging sensor system detection state with the other of the non-imaging sensor system detection state and the imaging sensor system detection state based on the non-imaging sensor system health state.

In addition to one or more of the features described above, or as an alternative, further embodiments of the flame or gas detection system may include that the instructions further cause the processor to determine an imaging sensor system detection state by receiving image data from an imaging sensor for the scene of interest; receiving an imaging sensor system keep-out definition for the scene of interest; and receiving imaging sensor system reference data for the scene of interest, the imaging sensor system detection state based on the image data from the imaging sensor, the imaging sensor system keep-out definition, and the imaging sensor system reference data for the scene of interest.

In addition to one or more of the features described above, or as an alternative, further embodiments of the flame or gas detection system may include that the imaging sensor system includes one of an infrared waveband imaging sensor and a visible light waveband imaging sensor.

In addition to one or more of the features described above, or as an alternative, further embodiments of the flame or gas detection system may include that the processor to validate the imaging system detection state based on an imaging sensor system keep-out definition of the scene of interest.

In addition to one or more of the features described above, or as an alternative, further embodiments of the flame or gas detection system may include that the instructions further cause the processor to receive an imaging sensor system health state and validate the imaging sensor system detection state with the imaging sensor system health state.

In addition to one or more of the features described above, or as an alternative, further embodiments of the flame or gas detection system may include that the non-imaging sensor system is a mid-wave infrared non-imaging sensor system, and further comprising an ultraviolet non-imaging sensor system operatively associated with the processor.

In addition to one or more of the features described above, or as an alternative, further embodiments of the flame or gas detection system may include that the imaging sensor system is an infrared imaging sensor system, and further comprising a visible waveband imaging sensor system operatively associated with the processor.

A computer program product is also provided. The computer program product is tangibly embodied on a computer readable medium, the computer program product including instructions that cause the processor to perform operations including performing algorithms to determine a non-imaging sensor detection state for a scene of interest; performing algorithms to determine an imaging sensor detection state for the scene of interest; validating the one of the non-imaging sensor detection state and the imaging sensor detection state with the other of the non-imaging sensor detection state and the imaging sensor detection state; and indicating, at a user interface, a system detection state comprising the one of the non-imaging sensor detection state and the imaging sensor detection state.

Technical effects of the present disclosure include the capability to detect and validate the presence of flame or gas within a scene of interest using both non-imaging and imaging sensor data. In certain examples the present disclosure provides the capability to detect flame or gas to be detected within the scene of interest using sensor data with spatial specificity. In accordance with certain examples the present disclosure provides the capability to detect flame or gas within the scene of interest using sensor data with spatial specificity and validation. Technical effects additionally include the capability to detect flame or gas within the scene of interest using non-imaging and/or imaging sensor data according to location, e.g., within a keep-in region or a keep-out region of the scene of interest, of the flame or gas within the scene of interest.

BRIEF DESCRIPTION OF THE DRAWINGS

The following descriptions should not be considered limiting in any way. With reference to the accompanying drawings, like elements are numbered alike:

FIG. 4 is state and action table for the flame or gas detector of FIG. 3, showing examples of non-imaging sensor/imaging sensor state and action associations according to an implementation.

DETAILED DESCRIPTION

Figure 1:
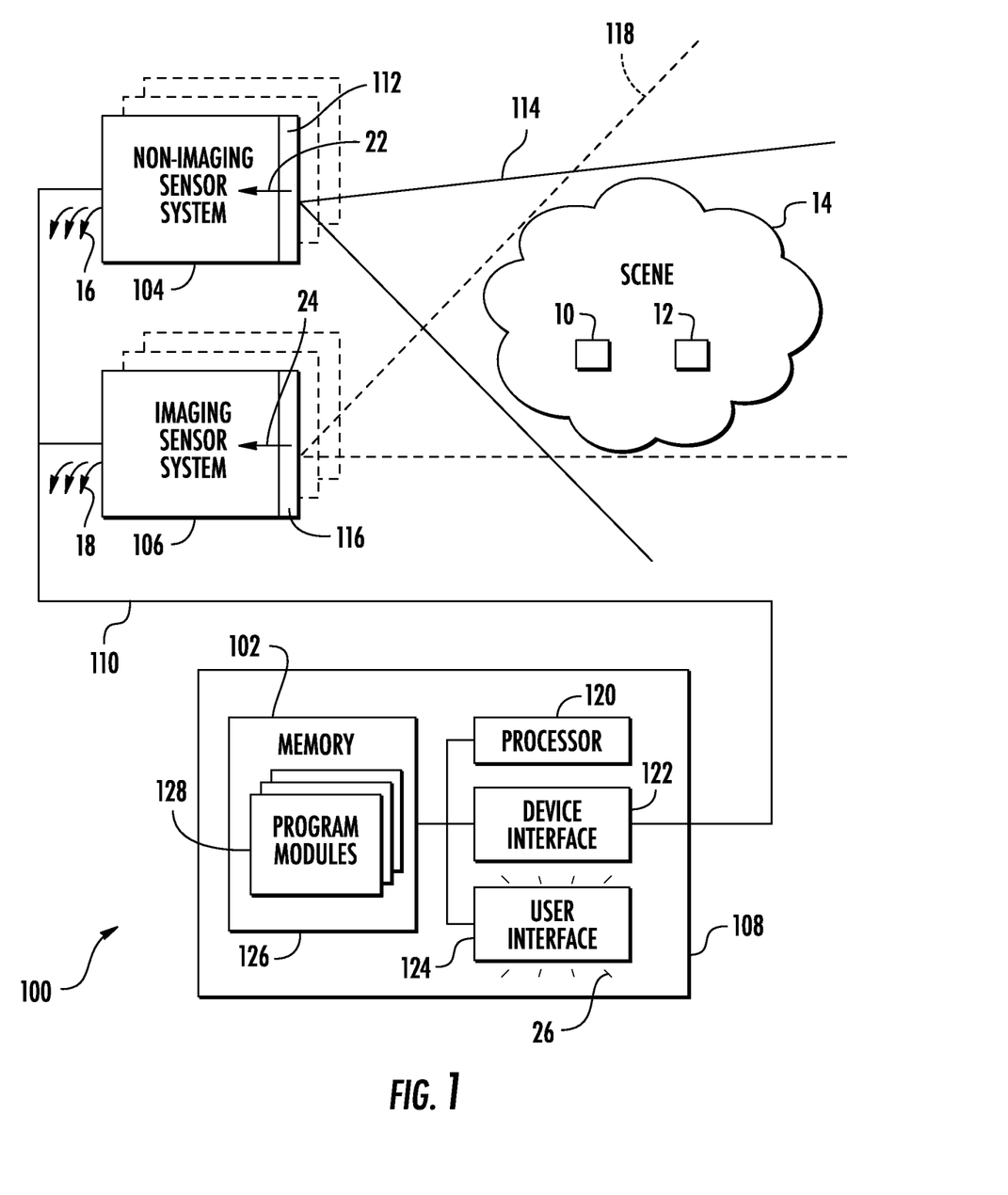
FIG. 1 is a schematic view of an example of a flame or gas detector constructed in accordance with the present disclosure, showing a controller disposed in communication with one or more non-imaging sensor systems and one or more imaging systems to determine whether flame or gas is present within a field of view of the non-imaging sensor system(s) and the imaging system(s)

Reference will now be made to the drawings wherein like reference numerals identify similar structural features or aspects of the subject disclosure. For purposes of explanation and illustration, and not limitation, a partial view of an example implementation of a flame or gas detector constructed in accordance with the disclosure is shown in FIG. 1 and is designated generally by reference character 100. Other embodiments of flame or gas detectors, flame or gas detection methods, and flame or gas detection algorithms, in accordance with the present disclosure, or aspects thereof, are provided in FIGS. 2-5, as will be described. The systems and methods described herein can be used for detecting and validating the presence of flame or gas in a scene of interest using both non-imaging sensor data and imaging data, such as from non-imaging sensor data and imaging data acquired from within a structure like a hanger, though the present disclosure is not limited to hangers or to stationary structures in general.

Flame or gas detection is typically accomplished using either non-imaging sensors or imaging sensors. Non-imaging sensors generally employ two or more non-imaging sensor components spectrally filtered to different sub-bands, e.g., within a mid-wave infrared waveband between about 2.5 microns and about 5 microns, and which output signals indicative of electromagnetic radiation within the different sub-bands. The signals output by such non-imaging sensors generally of indicate a detection state of the non-imaging sensor, i.e., whether the imaging sensor detects flame or gas and/or whether the imaging sensor does not detect flame or gas By spectrally tuning one or more of the sub-bands to include wavelengths where flame emits electromagnetic radiation (or gas absorbs electromagnetic radiation) such non-imaging sensors can generate signals containing information indicative of whether flame or gas is present within a scene. In the case of non-imaging sensors like thermopiles or pyroelectrics, strength of the signal generated by the sensors can be compared to a threshold known in the art to indicate the likely presences of flame or gas, and presence of flame or gas reported when the signal strength crosses the threshold.

Additionally, flame and gas typically do not present as constant, static phenomena, but rather fluctuate in intensity, and thus the detectable radiation (through emission or absorption) associated with the flame or gas also fluctuates over time within known frequency ranges over time, i.e. "flickers". Thus, the signal strength generated by the sensors can over time can be analyzed in the time/frequency domain, e.g., using flicker analysis, and presence of flame or gas reported when the time/frequency analysis indicates that flame or gas is present in the scene. While such non-imaging sensors are generally reliable, such non-imaging sensors are generally unable to provide sufficient spatial specificity to distinguish radiation absorption/emission sources generated in an area of interest from those adjacent to an area of interest, and therefore detection systems employing non-imaging sensors can generate false alarms—such as when a heat source like an engine moves in front of (or through) the scene of interest being monitored by the non-imaging sensor.

Imaging sensors, such as infrared imaging sensors and visible light (VL) imaging sensors, generally employ a camera-type device to discriminate between flame and non-flame sources in a scene of interest for purposes of providing a detection state, i.e., whether the imaging sensor detects flame or gas and/or whether the imaging sensor does not detect flame or gas. For example, infrared cameras can generate image data using electromagnetic radiation received within the infrared portion of the electromagnetic spectrum, and visible light cameras can generate image data using electromagnetic radiation received within the visible portion of the electromagnetic spectrum. Infrared images can be constructed from the infrared image data, visible images can be constructed from the visible light image data, and the infrared images and visible light images analyzed, e.g., using thresholding and/or with time/frequency analysis, to determine both whether flame or gas is present in the scene and, when flame or gas is present in the infrared image and/or visible light image, location of the flame or gas within the scene of interest. Such infrared and visible light imaging sensors are generally able to indicate flame or gas within a scene with some degree of confidence. However, some flame types and conditions can present challenges to such cameras, for example, due to flame translucency within the spectral bandpass of the imaging sensor and/or non-flame sources of electromagnetic energy within wavelengths of the spectral bandpass of the imaging sensor that may resemble flames.

As shown schematically in the exemplary flame/gas detector shown in FIG. 1, the flame or gas detector 100 is configured to detect a flame 10 or a gas 12 within a scene of interest 14, such as a hangar, using non-imaging sensor detection state(s) 16 and imaging sensor detection state(s) 18. The flame or gas detector 100 generally includes a controller 108 which in turn includes a computer program product 102 having instructions that, when read by a processor, e.g., the processor 120, cause the processor to perform operations including (a) determining the non-imaging sensor detection state(s) 16, (b) determining the imaging sensor detection state(s) 18, (c) deconflicting and validating one or more of the non-imaging sensor detection state(s) 16 and the imaging sensor detection state(s) 18 against the other of the detection states 16 and 18, and (d) indicating a system flame or gas detection state 26 that includes a validated detection state at a user interface 124, which may include a display and an input, examples may include a screen, a keyboard, touchscreen, joystick or mouse, and may also include audio output such as a speaker or sounder. Although the system flame or gas detection state 26 is shown as indicated at the user interface 124 it is to be understood and appreciated that the system flame or gas detection state 26 can be indicated other ways, like a signal communicated through a device interface, and remain within the scope of the present disclosure. Further, although shown and described herein in the context of a flame or gas detector 100 employed monitoring a scene of interest including a hanger, it is to be understood and appreciated that flame or gas detectors employed in other fixed structures, in defined outdoor spaces, and in vehicles can also benefit from the present disclosure.

In the example shown in FIG. 1 the flame or gas detector 100 includes a non-imaging sensor system 104, an imaging system 106, a controller 108, and a link 110. The link 110 may consist of one or more communication device(s) which may communicate using similar or different methods and/or protocols of communication, but for purposes of simplicity is referred to here as a singular communicative arrangement. It is contemplated that the link 110 can be a wired link or a wireless link, as suitable for an intended application. The link 110 communicatively connects the non-imaging sensor system 104 with the controller 108. The link 110 also communicatively connects the imaging system 106 with the controller 108. In certain examples the link 110 also communicatively connects the non-imaging sensor system 104 with the imaging system 106.

The non-imaging sensor system 104 includes one or more non-imaging sensor(s) 112. The non-imaging sensor(s) 112 have a non-imaging sensor field of view 114 and are configured to generate non-imaging sensor data 22 of a scene of interest within the sensor field of view 114, e.g., the scene of interest 14, the non-imaging sensor data 22 lacking positional information. The non-imaging sensor system 104 is operatively connected to the non-imaging sensor(s) 112 and is in turn configured to determine the sensor detection state(s) 16 using the non-imaging sensor data 22. In certain examples the non-imaging sensor(s) 112 include an ultra-violet sensor. In accordance with certain examples the non-imaging sensor(s) 112 include a mid-wave infrared spectral (MWIR) sensor.

The imaging system 106 includes one or more imaging sensor(s) 116. The imaging sensor(s) 116 have an imaging sensor field of view 118 and are configured to generate imaging sensor data 24 including position information of a scene of interest within the imaging sensor field of view 118, e.g., the scene of interest 14. The imaging system 106 is operatively connected to the imaging sensor(s) 116 and is in turn configured to determine the imaging sensor detection state(s) 18 using the imaging sensor data 24. In certain examples the imaging sensor(s) 116 includes an infrared focal plane array. In other examples the imaging sensor(s) 116 include a visible light focal plane array.

It is contemplated that some or all of the imaging systems(s) 116 and non-imaging system(s) 112 overlap such that even though the fields of view, 114, 118 may not be exactly the same, each overlaps all or a portion of another system's field of view 114, 118 and the scene of interest 14, such that they can be combined to fully overlap the scene of interest. It also is contemplated that the imaging system(s) 116 have known spatial registrations to one another such that even though the fields of view might not be aligned, the information from the imaging system(s) 116 can still be combined with one another with spatial specificity. Likewise, it is contemplated that the non-imaging system(s) 112 have known spatial alignment to one another such that even though the fields of view might not be aligned, the information from the non-imaging system(s) 112 can still be combined with one another with spatial specificity. Likewise, it is contemplated that the imaging system(s) 116 and the non-imaging system(s) 112 have known spatial registrations to one another such that even though the fields of view might not be aligned, the information from the imaging system(s) 116 and the non-imaging system(s) 112 can still be combined with one another with spatial specificity.

The controller 108 includes a processor 120, a device interface 122, a user interface 124, and a memory 126. The device interface 122 connects the controller 108 to the non-imaging sensor system 104 and the imaging system 106 through the link 110. The processor 120 is connected to the device interface 122 for communication therethrough with the non-imaging sensor system 104 and the imaging system 106. The processor 120 is also operably connected to the user interface 124 and is disposed in communication with the memory 126. As shown in FIG. 1 the computer program product 102 is tangibly embodied on the memory 126, which includes a non-transitory machine-readable medium having a plurality of program modules 128 recorded thereon that, when read by the processor, cause the process to execute certain operations. Among those operations are operations of a flame or gas detection method 200, as will be described. It is contemplated that the controller 108 can be implemented using software, circuitry, or a combination of software and circuitry, as suitable for an intended application.

Figure 2:
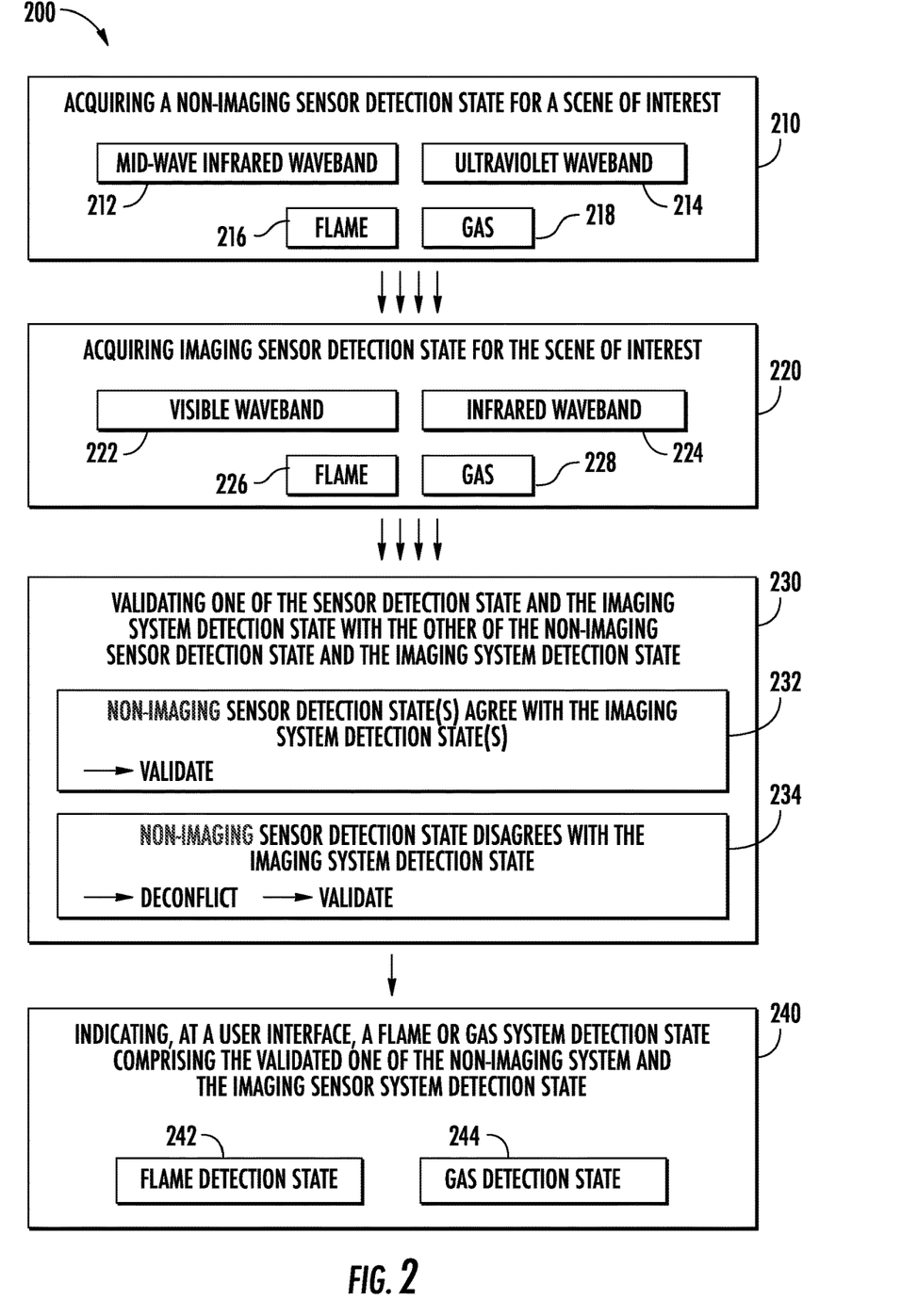
FIG. 2 is a block diagram of a flame or gas detection method in accordance with the present disclosure, showing steps of the method according to an illustrative and non-limiting example of the method.

With reference to FIG. 2, the flame or gas detection method 200 is shown. As shown with box 210, the flame or gas detection method 200 includes determining non-imaging sensor detection state(s), e.g., the sensor detection state(s) 16 (shown in FIG. 1). In certain examples the non-imaging sensor detection state(s) are determined using electromagnetic radiation received at a non-imaging sensor, e.g., the non-imaging sensor(s) 112 (shown in FIG. 1), in one or more MWIR wavebands, as shown with box 212. In accordance with certain examples the non-imaging sensor detection state(s) are determined using electromagnetic radiation received at the non-imaging sensor in an ultraviolet waveband, as shown with box 214. The non-imaging sensor analyzes the electromagnetic radiation received by the non-imaging sensor and determines the detection state of the non-imaging sensor, i.e., flame presence or absence state(s), as shown with box 216. It is also contemplated that the non-imaging sensor detection state(s) can be gas presence or absence state(s), as shown with box 218.

As shown with box 220, the flame or gas detection method 200 also includes determining imaging sensor detection state(s), e.g., the imaging sensor detection state(s) 18 (shown in FIG. 1). In certain examples the imaging sensor detection state(s) are determined using electromagnetic radiation received at imaging sensor(s), e.g., the imaging sensor(s) 116 (shown in FIG. 1), in a visible waveband, as shown with box 222. In accordance with certain examples the imaging sensor detection state(s) are determined using electromagnetic radiation received at the imaging sensor(s) in an infrared waveband, as shown with box 224. The imaging sensor analyzes the electromagnetic radiation received by the non-imaging sensor and determines the detection state of the imaging sensor, i.e., flame presence or absence state(s), as shown with box 226. It is also contemplated that the imaging sensor detection state(s) can be gas presence or absence state(s), as shown with box 228.

As shown with box 230, the flame or gas detection method 200 additionally includes deconflicting and validating one or more of the sensor detection state(s) and the non-imaging sensor detection state(s) with the other of the sensor detection state(s) and the imaging sensor detection state(s). When the non-imaging sensor detection state(s) agree with the imaging sensor detection state(s), the validated detection state is indicated at a user interface, e.g., the user interface 124 (shown in FIG. 1), as a system flame or gas detection state, e.g., the system flame or gas detection state 26 (shown in FIG. 1), as shown with boxes 232 and 240. When the non-imaging detection state(s) disagree with the imaging sensor detection state(s) the disagreement is deconflicted, and the deconflicted detection state indicated at a user interface, e.g., the user interface 124 (shown in FIG. 1), as a system flame or gas detection state, e.g., the system flame or gas detection state 26 (shown in FIG. 1), as shown with boxes 234 and 240. Indication can be accomplished, for example, visually or audibly. Deconfliction can be accomplished using one or more of a sensor health status, an imaging sensor health status, sensor reference data, imaging sensor reference data, and/or application of a keep-in or keep-out definition in conjunction with the imaging sensor data as described further below with reference to FIGS. 3-5.

For example, a scene of interest can be imaged and image divided into one or more image portions wherein indication of flame or gas is disregarded for purposes of determining the imaging sensor detection state, and into one or more image portion wherein indication of flame or gas is considered for purposes of the imaging sensor detection state. In certain examples the system flame or gas detection state is a flame detection state, as shown with box 242. In accordance with certain examples the system flame or gas detection state is a gas detection state, as shown with box 244.

Figure 3:
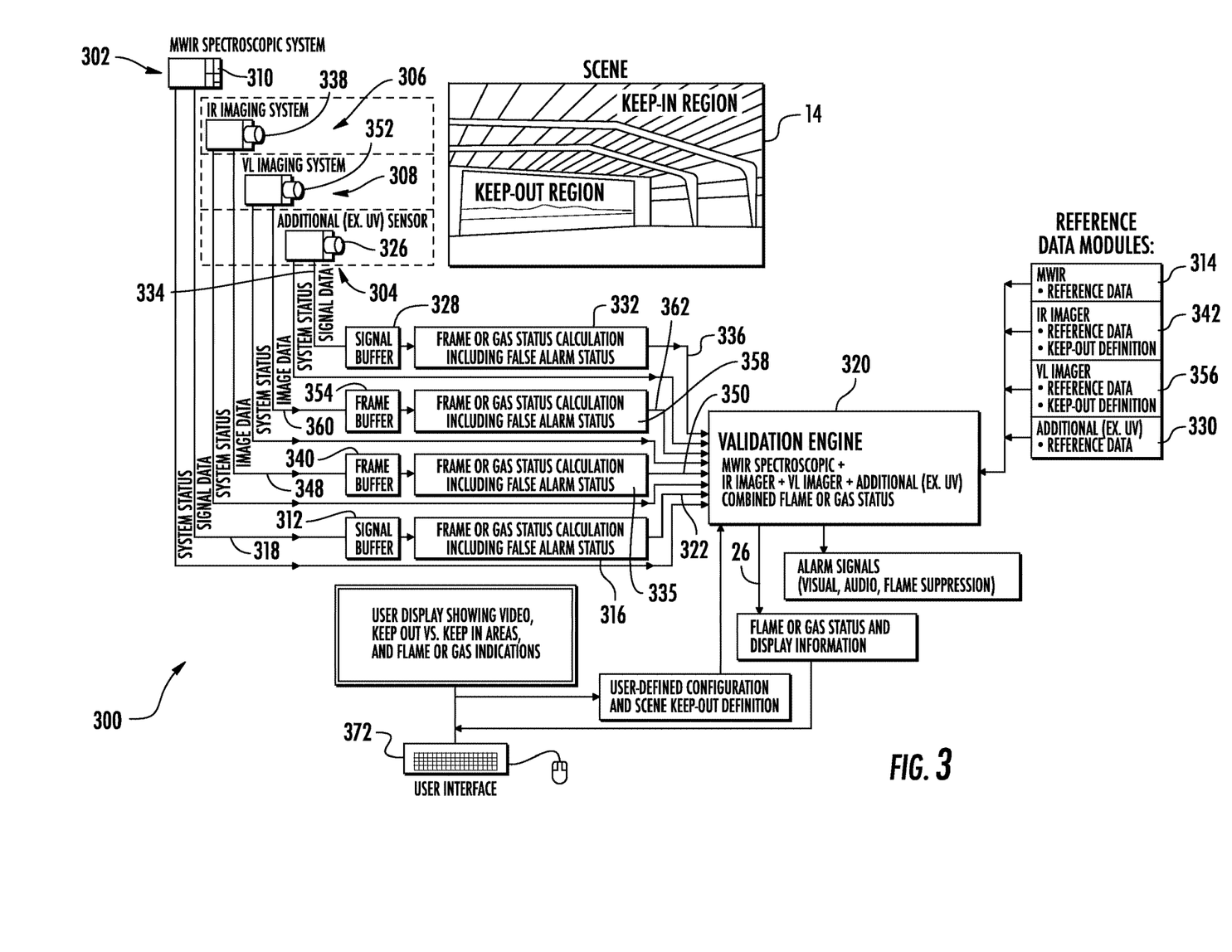
FIG. 3 is schematic view of a flame or gas detector according to another example of the flame or gas detector of FIG. 1, showing a flame or gas detector having a plurality of non-imaging sensors and a plurality of imaging sensors.

With reference to FIG. 3, a flame or gas detector 300 is shown. The flame or gas detector 300 is similar to the flame or gas detector 100 (shown in FIG. 1) and additionally includes a plurality of non-imaging sensor systems, e.g., an MWIR non-imaging sensor system 302 and an ultraviolet non-imaging sensor 304. The flame or gas detector 300 also includes a plurality of imaging sensor systems, e.g., an infrared imaging system 306 and a visible light imaging system 308. The flame or gas detector 300 additionally includes a validation engine 320 for deconflicting and validating one or more of the non-imaging sensor detection state(s) 16 and the imaging sensor detection state(s) 18 against the other of the detection states 16 and 18. Although a specific group of non-imaging sensor systems and imaging sensor systems are shown in the illustrated example it is to be understood that flame or gas detectors having different, fewer or additional non-imaging sensor systems and imaging sensor systems are within the scope of the present disclosure.

The MWIR non-imaging sensor system 302 includes an MWIR non-imaging sensor array 310, an MWIR sensor signal buffer 312, an MWIR sensor reference data module 314, and an MWIR sensor detection state determination module 316. The MWIR non-imaging sensor array 310 is configured to acquire MWIR non-imaging sensor data 318 of the scene of interest 14. The MWIR sensor signal buffer 312 is disposed in communication with MWIR non-imaging sensor array 310 to receive therefrom the MWIR non-imaging sensor data 318, and is further configured to buffer the MWIR non-imaging sensor data 318 according to a schedule in order to synchronize delivery of the MWIR non-imaging sensor data 318 to the validation engine 320 with the one or more data 348, 360, and/or 334 from the plurality of non-imaging sensor systems and/or the imaging sensor systems 338, 352, and/or 326 of the flame or gas detector 300. The MWIR sensor detection state determination module 316 is disposed in communication with the MWIR sensor signal buffer 312 to receive therefrom the MWIR non-imaging sensor data 318 and is configured to determine an MWIR non-imaging sensor detection state 322 from the MWIR non-imaging sensor data 318.

It is contemplated that the MWIR sensor reference data module 314 employ a process for verifying or adjusting algorithm parameters based on scene content. For example, a scene of interest having a known flame or gas condition (i.e. a flame or gas with known characteristics such as intensity and luminosity generated for the purpose of characterization) can be observed over a period of time while the MWIR non-imaging sensor system 302 executes flame or gas detection operations for the purpose of verifying the range of metrics associated with the known flame or gas condition. In one such case, the scene of interest is monitored by the MWIR non-imaging sensor system 302 for a period of time while no flame is present and metrics are calculated using the MWIR sensor data and recorded into a memory, such as memory 126. The metrics are used to verify or adjust the detection threshold (or thresholds) and provide the MWIR non-imaging sensor system 302 a metrics-based definition of the scene of interest 14 when no flame is present. In another case the scene of interest 14 is observed over a period of time during which a known flame is within the scene of interest 14, metrics recorded in a memory and calculated using the MWIR sensor data, and the calculated metrics are used to verify or adjust the detection threshold (or thresholds) and provide the MWIR non-imaging sensor system 302 a metrics-based definition of the scene of interest when a known flame is present.

The ultraviolet non-imaging sensor system 304 includes an ultraviolet non-imaging sensor 326, an ultraviolet sensor signal buffer 328, an ultraviolet non-imaging sensor reference module 330, and an ultraviolet sensor detection state determination module 332. The ultraviolet non-imaging sensor 326 is configured to acquire ultraviolet non-imaging sensor data 334 of the scene of interest 14. The ultraviolet sensor signal buffer 328 is disposed in communication with the ultraviolet non-imaging sensor 326 to receive therefrom the ultraviolet non-imaging sensor data 334, and is further configured to buffer the ultraviolet non-imaging sensor data 334 according to a schedule in order to synchronize delivery of the ultraviolet non-imaging sensor data 334 to the validation engine 320 with the one or more data 318, 348, and/or 360 from the plurality of non-imaging sensors and/or imaging sensors 310, 338, and/or 352 of the flame or gas detector 300. The ultraviolet sensor detection state determination module 332 is disposed in communication with the ultraviolet sensor signal buffer 328 to receive therefrom the ultraviolet non-imaging sensor data 334 and is further configured to determine an ultraviolet non-imaging sensor detection state 336 from the ultraviolet non-imaging sensor data 334.

The infrared imaging system 306 includes an infrared focal plane array 338, an infrared imaging system frame buffer 340, an infrared imaging system reference module 342, and an infrared imaging system detection state determination module 335. The infrared focal plane array 338 is configured to acquire infrared image data 348 of the scene of interest 14. The infrared imaging system frame buffer 340 is disposed in communication with the infrared focal plane array 338 to receive therefrom the infrared image data 348, and is further configured to buffer the infrared image data 348 according to a schedule in order to synchronize delivery of the infrared image data 348 to the validation engine 320 with the one or more data 318, 360, and/or 334 from the plurality of non-imaging sensors and/or imaging sensors 310, 352, and/or 326 of the flame or gas detector 300. The infrared imaging system detection state determination module 335 is disposed in communication with the infrared imaging system frame buffer 340 to receive therefrom the infrared image data 348 and is configured to determine an infrared imaging system detection state 350 from the infrared image data 348.

The visible light imaging system 308 includes a visible light focal plane array 352, a visible light imaging system frame buffer 354, a visible light imaging system reference module 356, and a visible light imaging system detection state determination module 358. The visible light focal plane array 352 is configured to acquire visible light imaging system data 360 of the scene of interest 14. The visible light imaging system frame buffer 354 is disposed in communication with the visible light focal plane array 352 to receive therefrom the visible light imaging system data 360, and is further configured to buffer the visible light imaging system data 360 according to a schedule in order to synchronize delivery of the visible light imaging system data 360 to the validation engine 320 with one or more data of data 318, 348, and/or 334 from the plurality of non-imaging sensors and/or imaging sensors 310, 338, and/or 326 of the flame or gas detector 300. The visible light imaging system detection state determination module 358 is disposed in communication with the visible light imaging sensor frame buffer 354 to receive therefrom the visible light imaging system data 360 and is configured to determine a visible light imaging system detection state 362 from the visible light imaging system data 360.

The validation engine 320 is further configured to determine the flame or gas detection state 26 using state-specific analysis and decision making according to associations of system state scenarios and validation engine actions stored in memory such as the memory 126, for example, in a state table or other suitable storage format. FIG. 4 shows an illustrative example of association of system state scenarios 364 and validation engine actions 366. In this respect the validation engine 320 is disposed in communication with each of the plurality of non-imaging sensors, e.g., the MWIR non-imaging sensor system 302 and the ultraviolet non-imaging sensor system 304, to receive therefrom a health status (shown in FIG. 5) and a detection status of the respective non-imaging system. In further respect the validation engine 320 is also disposed in communication with each of the plurality of imaging systems, e.g., the infrared imaging system 306 and the visible light imaging system 308. The validation engine 320 is configured such that certain sub-systems take precedent, e.g., non-imaging systems and/or imaging systems with acceptable health states, in determining appropriate engine actions 366 according to scenarios which may be discerned from the full set of sub-system states. The set of example system states and appropriate actions in FIG. 4 are chosen according to known detection susceptibilities of each sub-system type such that the most robust flame or gas detection can occur, e.g., by validating an infrared flame candidate in infrared imagery using an infrared intensity associated with a frequency reported by the MWIR non-imaging sensor. In general, the validation engine actions 366 may be application-configurable according to known conditions (structures that emit at wavebands tending to provoke false alarms from one or more of the imaging sensors and non-imaging sensors) or predisposed hazards (potential location of flame or gas source) in the specific installation environment.

Figure 5:
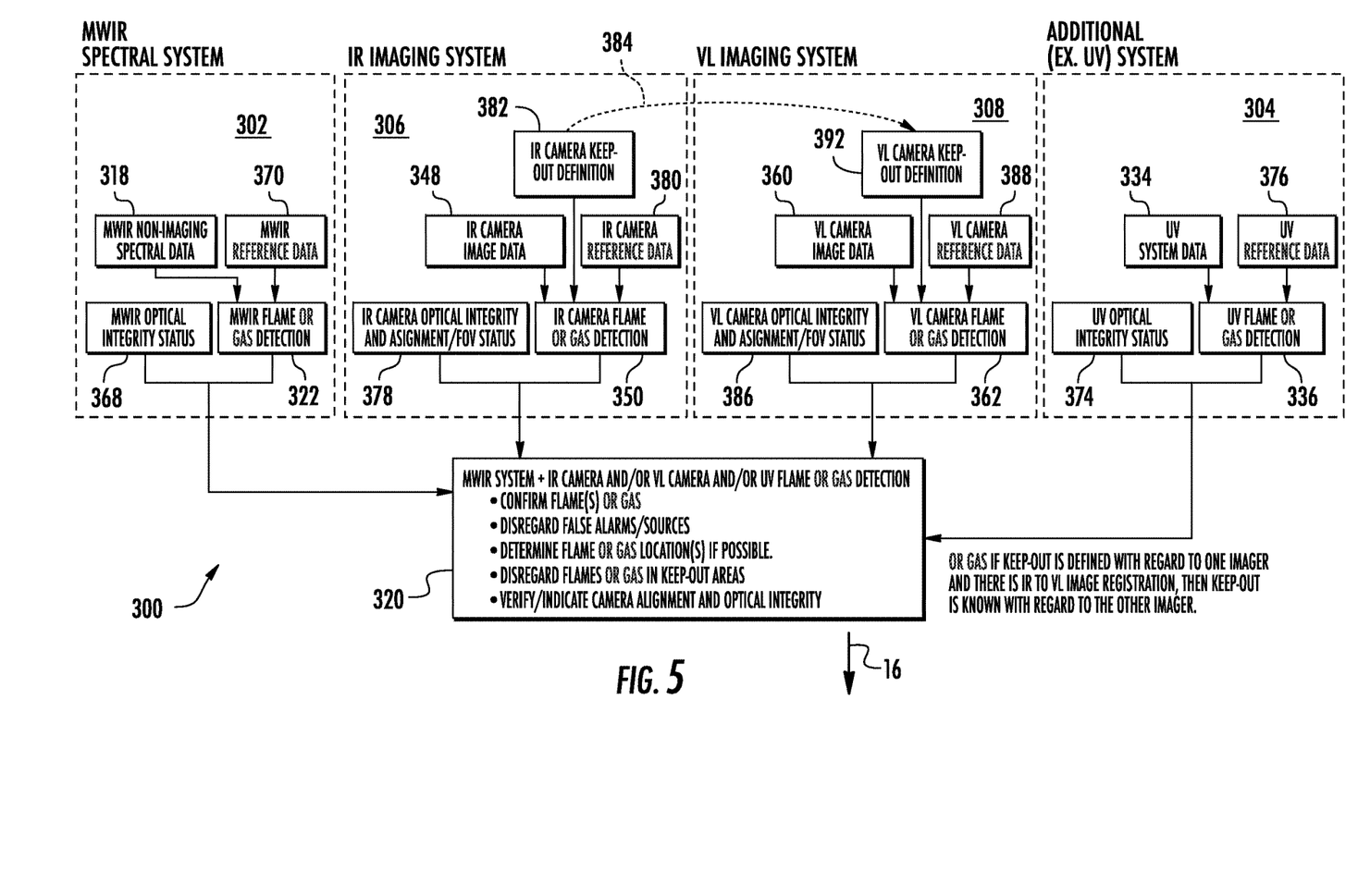
FIG. 5 is a block diagram of data flows within the flame or gas detector of FIG. 3, showing types of data used by the non-imaging sensors and imaging sensors to determine the non-imaging sensor and the imaging sensor detection states according to an implementation.

With reference to FIG. 5, data flows through a portion of the flame or gas detector 300 are shown. As shown within the MWIR non-imaging sensor system 302, an MWIR non-imaging sensor health status 368 and the MWIR non-imaging sensor detection state 322 are determined by the MWIR non-imaging sensor system 302. The MWIR non-imaging sensor health status 368 in turn indicates whether the MWIR non-imaging sensor detection state 322 should be included or excluded (disregarded) by the validation engine 320 in determining the flame or gas detection state 26. In certain examples an on-board diagnostics module can determine the MWIR non-imaging sensor health status 368.

The MWIR non-imaging sensor detection state 322 is determined using MWIR non-imaging sensor data 318 acquired by the MWIR non-imaging sensor array 310 (shown in FIG. 3) in conjunction with the MWIR sensor system reference data 370 received from the MWIR sensor reference module data 314 (shown in FIG. 3). In certain examples the MWIR sensor system reference data 370 is user defined, e.g., thresholding information and/or frequency characterization received through a user interface, e.g., a user interface 372 (shown in FIG. 3). In accordance with certain examples the MWIR sensor system reference data 370 may also be acquired by monitoring scene content as described above with respect to the process for verifying or adjusting algorithm parameters based on scene content.

As shown within the ultraviolet non-imaging sensor system 304, an ultraviolet non-imaging sensor health status 374 and the ultraviolet non-imaging sensor detection state 336 are determined by the ultraviolet non-imaging sensor system 304. The ultraviolet non-imaging sensor health status 374 indicates whether the ultraviolet non-imaging sensor detection state 336 should be included or excluded (disregarded) by the validation engine 320 in determining the flame or gas detection state 26. In certain examples an on-board diagnostics module determines the ultraviolet non-imaging sensor health status 374.

The ultraviolet non-imaging sensor detection state 336 is determined using the ultraviolet non-imaging sensor data 334, which is acquired by the ultraviolet non-imaging sensor 326 (shown in FIG. 3) in conjunction with the ultraviolet sensor system reference data 376 received from the ultraviolet non-imaging sensor reference module 330 (shown in FIG. 3). In certain examples the ultraviolet sensor system reference data 376 is user defined, e.g., thresholding information and/or frequency characterization received through the user interface 372 (shown in FIG. 3). In accordance with certain examples the ultraviolet sensor system reference data 376 may be acquired by monitoring scene content as described above with respect to the process for verifying or adjusting algorithm parameters based on scene content (which may be applied to ultraviolet non-imaging sensors in a similar manner as described for verifying or adjusting algorithm parameters for MWIR sensors).

As shown within the infrared imaging system 306, an infrared imaging system health status 378 and the infrared imaging system detection state 350 are determined by the infrared imaging system 306. The infrared imaging system health status 378 indicates whether the infrared imaging system detection state 350 should be included or excluded (disregarded) by the validation engine 320 in determining the flame or gas detection state 26. In certain examples an on-board diagnostics module determines the infrared imaging system health status 378.

The infrared imaging system detection state 350 is determined using the infrared image data 348 from the infrared focal plane array 338 (shown in FIG. 3) in conjunction with infrared imaging system reference data 380, an infrared imaging system keep-out definition 382, and cross-referencing data 384. The infrared imaging system reference data 380 is received from the infrared imaging system reference module 342 (shown in FIG. 3) and may be received from a user interface, e.g., the user interface 372 (shown in FIG. 3), and/or acquired using scene monitoring operations as described above with respect to the process for verifying or adjusting algorithm parameters based on scene content (which may be applied to infrared imaging system sensors in a similar manner as described for verifying or adjusting algorithm parameters for MWIR sensors). The infrared imaging system keep-out definition 382 demarcates, e.g., established during set up of the flame or gas detection system, image data frames received from the infrared imaging system frame buffer 340 (shown in FIG. 3) into frame regions where flame indication is eligible for determining the flame or gas detection state 26 and frame regions where flame indication is ineligible for determining the flame or gas detection state 26. The cross-referencing data 384 is received from one or more non-imaging sensor and/or imaging sensor and provides additional checks to the validity of the infrared imaging system detection state 350 specific to a given system/system pair and/or system/sensor pair, when the imaging system receives electromagnetic radiation in a waveband associated with false detection events is the non-imaging sensor.

As shown within the visible light imaging system 308, a visible light imaging system health status 386 and the visible light imaging system detection state 362 are determined by the visible light imaging system 308. The visible light imaging system health status 386 indicates whether the visible light imaging sensor detection state 362 should be included or excluded (disregarded) by the validation engine 320 in determining the flame or gas detection state 26. In certain examples an on-board diagnostics module determines the visible light imaging system health status 386.

The visible light imaging system detection state 362 is determined using the visible light imaging sensor data 360 from the visible light focal plane array 352 (shown in FIG. 3) in conjunction with visible light imaging system reference data 388, a visible imaging system keep-out definition 392, and cross-referencing data 384. The visible imaging system reference data 388 is received from the visible light imaging system reference module 356 (shown in FIG. 3) and may be received from a user interface, e.g., the user interface 372 (shown in FIG. 3), and/or acquired using scene monitoring operations as described above with respect to the process for verifying or adjusting algorithm parameters based on scene content (which may be applied to VL imaging system sensors in a similar manner as described for verifying or adjusting algorithm parameters for MWIR sensors). The visible imaging system keep-out definition 392 demarcates image data frames received from the visible light imaging system frame buffer 354 (shown in FIG. 3) into frame region where flame indication is eligible for determining the flame or gas detection state 26 and frame regions where flame indication is ineligible for determining the flame or gas detection state 26.

The present disclosure provides techniques for combining data from imaging systems (including visible light and infrared imaging sensors) with data from non-imaging systems (including mid-wave infrared non-imaging sensors) in order to more reliably detect and validate the occurrence of flame or gas, to indicate the flame or gas location via image data, to disregard flame or gas that is detected in areas that are meant to be unmonitored, (sometimes referred to as 'keep-out regions'), and to minimize the occurrence of false alarms as compared to a system that utilizes imaging or non-imaging technology exclusively.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A flame or gas detection method, comprising:
determining a non-imaging sensor system detection state for a scene of interest;
determining an imaging sensor system detection state for the scene of interest;
validating one of the non-imaging sensor system detection state and the imaging sensor system detection state with the other of the non-imaging sensor system detection state and the imaging sensor system detection state; and
indicating, at a user interface, a flame or gas detection system detection state including the validated one of the non-imaging sensor system detection state and the imaging sensor system detection state;
wherein determining the imaging sensor system detection state includes:
receiving image data from an imaging sensor for the scene of interest;
receiving imaging sensor system reference data for the scene of interest;
receiving an imaging sensor system keep-out definition for the scene of interest, the keep-out definition demarcating image data frames of the image data into a frame region where flame indication is eligible for determining the flame or gas detection state and frame regions where flame indication is ineligible for determining the flame or gas detection state; and determining the imaging sensor system detection state based on the image data from the imaging sensor, the imaging sensor system reference data, and the imaging sensor system keep-out definition for the scene of interest.

2. The detection method of claim 1, wherein determining the non-imaging sensor system detection state includes:
receiving non-imaging sensor data for the scene of interest;
receiving non-imaging sensor system reference data for the scene of interest; and
determining the non-imaging sensor system detection state based on the non-imaging sensor data and the non-imaging sensor system reference data for the scene of interest.

3. The detection method of claim 2, further comprising generating the non-imaging sensor data from electromagnetic radiation incident on a non-imaging sensor in a mid-wave infrared waveband or an ultraviolet waveband.

4. The detection method of claim 2, further comprising receiving a non-imaging sensor system health state, wherein the validating one of the non-imaging sensor system detection state and the imaging sensor system detection state with the other of the non-imaging sensor system detection state and the imaging sensor system detection state is based on the non-imaging sensor system health state.

5. The method of claim 1, further comprising generating the image data from electromagnetic radiation incident on an imaging sensor in an infrared waveband or a visible light waveband.

6. The method of claim 1, wherein validating one of the non-imaging sensor system detection state and the imaging sensor system detection state with the other of the non-imaging sensor system detection state and the imaging sensor system detection state is based on the imaging sensor system keep-out definition for the scene of interest.

7. The method of claim 1, further comprising receiving an imaging sensor system health status, wherein validating one of the non-imaging sensor system detection state and the imaging sensor system detection state with the other of the non-imaging sensor system detection state and the imaging sensor system detection state is based on the imaging sensor system health state.

8. The method of claim 1, wherein the non-imaging sensor system detection state and the imaging sensor detection state are a non-imaging sensor system flame detection state and an imaging sensor system flame detection state.

9. The method of claim 1, wherein the non-imaging sensor system detection state and the imaging sensor system detection state are a non-imaging sensor system gas detection state and an imaging sensor system gas detection state.

10. A flame or gas detection system, comprising:
a non-imaging sensor system with a non-imaging sensor field of view including a scene of interest;
an imaging sensor system with an imaging sensor field of view including the scene of interest; and
a processor disposed in communication with the non-imaging sensor system, the imaging sensor system, and a memory having instructions recorded on the memory that, when executed by the processor, cause the processor to:
determine a non-imaging sensor system detection state for the scene of interest;
determine an imaging sensor system detection state for the scene of interest;
validate one of the non-imaging sensor system detection state and the imaging sensor system detection state with the other of the non-imaging sensor system detection state and the imaging sensor system detection state; and
indicate, at a user interface operatively associated with the processor, a flame or gas detection system detection state comprising the validated one of the non-imaging sensor system detection state and the imaging sensor system detection state;
wherein determining the imaging sensor system detection state includes:
receiving image data from an imaging sensor for the scene of interest;
receiving imaging sensor system reference data for the scene of interest;
receiving an imaging sensor system keep-out definition for the scene of interest, the keep-out definition demarcating image data frames of the image data into a frame region where flame indication is eligible for determining the flame or gas detection state and frame regions where flame indication is ineligible for determining the flame or gas detection state; and
determining the imaging sensor system detection state based on the image data from the imaging sensor, the imaging sensor system reference data, and the imaging sensor system keep-out definition for the scene of interest.

11. The system of claim 10, wherein the instructions further cause the processor to determine the non-imaging sensor system detection state by:
receiving non-imaging sensor data from a non-imaging sensor for the scene of interest;
receiving non-imaging sensor reference data for the scene of interest; and
determining the non-imaging sensor system detection state based on the non-imaging sensor data and the non-imaging sensor reference data for the scene of interest.

12. The system of claim 10, wherein the non-imaging sensor is a mid-wave infrared waveband sensor or an ultraviolet waveband sensor.

13. The system of claim 10, wherein the instructions further cause the processor to receive a non-imaging sensor system health state, wherein the processor validates the one of the non-imaging sensor system detection state and the imaging sensor system detection state with the other of the non-imaging sensor system detection state and the imaging sensor system detection state based on the non-imaging sensor system health state.

14. The system of claim 10, wherein the imaging sensor system includes one of an infrared waveband imaging sensor and a visible light waveband imaging sensor.

15. The system of claim 10, wherein the instructions further cause the processor to validate the imaging system detection state based on an imaging sensor system keep-out definition of the scene of interest.

16. The system of claim 10, wherein the instructions further cause the processor to receive an imaging sensor system health state and validate the imaging sensor system detection state with the imaging sensor system health state.

17. The system of claim 10, wherein the non-imaging sensor system is a mid-wave infrared non-imaging sensor system, and further comprising an ultraviolet non-imaging sensor system operatively associated with the processor.

18. The system of claim 10, wherein the imaging sensor system is an infrared imaging sensor system, and further comprising a visible waveband imaging sensor system operatively associated with the processor.

19. A computer program product tangibly embodied on a non-transitory computer readable medium, the computer program product including instructions that, when executed by a processor, cause the processor to perform operations comprising:
  performing algorithms to determine a non-imaging sensor detection state for a scene of interest;
  performing algorithms to determine an imaging sensor detection state for the scene of interest;
  validating the one of the non-imaging sensor detection state and the imaging sensor detection state with the other of the non-imaging sensor detection state and the imaging sensor detection state; and
  indicating, at a user interface, a system detection state comprising the one of the non-imaging sensor detection state and the imaging sensor detection state;
  wherein determining the imaging sensor system detection state includes:
    receiving image data from an imaging sensor for the scene of interest;
    receiving imaging sensor system reference data for the scene of interest;
    receiving an imaging sensor system keep-out definition for the scene of interest, the keep-out definition demarcating image data frames of the image data into a frame region where flame indication is eligible for determining the flame or gas detection state and frame regions where flame indication is ineligible for determining the flame or gas detection state; and
    determining the imaging sensor system detection state based on the image data from the imaging sensor, the imaging sensor system reference data, and the imaging sensor system keep-out definition for the scene of interest.

* * * * *